US006938470B2

(12) United States Patent
DiFoggio et al.

(10) Patent No.: US 6,938,470 B2
(45) Date of Patent: Sep. 6, 2005

(54) METHOD AND APPARATUS FOR DOWNHOLE FLUID CHARACTERIZATION USING FLEXURAL MECHANICAL RESONATORS

(75) Inventors: Rocco DiFoggio, Houston, TX (US); Arnold Walkow, Houston, TX (US); Paul Bergren, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 10/144,965

(22) Filed: May 14, 2002

(65) Prior Publication Data

US 2002/0178805 A1 Dec. 5, 2002

Related U.S. Application Data

(60) Provisional application No. 60/291,136, filed on May 15, 2001.

(51) Int. Cl.[7] .............................. G01H 3/04; G01H 3/14
(52) U.S. Cl. ................ 73/152.24; 73/54.41; 73/152.16; 73/152.47; 73/152.58; 175/40; 175/50
(58) Field of Search ......................... 73/152.55, 152.58, 73/24.06, 61.62, 152.14, 152.16, 152.47, 152.52; 166/264; 175/40, 48, 56; 367/27, 81

(56) References Cited

U.S. PATENT DOCUMENTS

| 3,130,808 A | * | 4/1964 | Walker et al. ................ 367/27 |
| 3,346,058 A | * | 10/1967 | Bouyoucos ................. 175/56 |
| 3,390,737 A | * | 7/1968 | Johnson ...................... 181/106 |
| 3,449,940 A | | 6/1969 | Banks | |
| 3,608,715 A | | 9/1971 | Snyder et al. | |
| 3,760,204 A | * | 9/1973 | Yester, Jr. ................ 310/313 B |
| 3,903,732 A | | 9/1975 | Rork et al. | |
| 4,526,480 A | | 7/1985 | Ward | |
| 4,574,639 A | | 3/1986 | Ward | |

(Continued)

FOREIGN PATENT DOCUMENTS

| EP | 0 282 251 B1 | 2/1993 | |
| JP | 63151837 A | * 6/1988 | ............ G01N/9/00 |
| WO | WO 02/099414 | 12/2002 | |

OTHER PUBLICATIONS

Calhoun, John C., Fundementals of Reservoir Engineering, 1953, pp. 34–42.
Predicting the Viscosity of Natural Gas, International Journal of Thermophysics, vol. 22, No. 2, 2001. pp. 415–417.

(Continued)

Primary Examiner—Hezron Williams
Assistant Examiner—David A. Rogers
(74) Attorney, Agent, or Firm—Madan, Mossman & Sriram, P.C.

(57) ABSTRACT

The present invention provides a downhole method and apparatus using a flexural mechanical resonator, for example, a tuning fork to provide real-time direct measurements and estimates of the viscosity, density and dielectric constant of formation fluid or filtrate in a hydrocarbon producing well. The present invention additionally provides a method and apparatus for monitoring cleanup from a leveling off of viscosity or density over time, measuring or estimating bubble point for formation fluid, measuring or estimating dew point for formation fluid, and determining the onset of asphaltene precipitation. The present invention also provides for intercalibration of plural pressure gauges used to determine a pressure differential downhole.

30 Claims, 7 Drawing Sheets

U.S. PATENT DOCUMENTS

| | | | |
|---|---|---|---|
| 4,602,505 A | | 7/1986 | Kanda et al. |
| 4,679,427 A | | 7/1987 | Kanda et al. |
| 4,729,237 A | | 3/1988 | Suzuki et al. |
| 4,922,745 A | | 5/1990 | Rudkin et al. |
| 5,006,845 A | * | 4/1991 | Calcar et al. ................. 367/81 |
| 5,048,351 A | | 9/1991 | Dames |
| 5,204,529 A | * | 4/1993 | Diatschenko ............... 250/268 |
| 5,269,188 A | * | 12/1993 | Esin et al. .................... 73/610 |
| 5,361,632 A | * | 11/1994 | Magnani .................. 73/152.14 |
| 5,622,223 A | * | 4/1997 | Vasquez ..................... 166/264 |
| 5,734,098 A | * | 3/1998 | Kraus et al. ............... 73/61.62 |
| 5,741,962 A | * | 4/1998 | Birchak et al. .......... 73/152.16 |
| 5,837,893 A | * | 11/1998 | Chu ........................ 73/152.52 |
| 6,073,492 A | * | 6/2000 | Rosselson et al. ............. 73/644 |
| 6,128,949 A | * | 10/2000 | Kleinberg ................ 73/152.18 |
| 6,176,323 B1 | * | 1/2001 | Weirich et al. ................ 175/40 |
| 6,182,499 B1 | * | 2/2001 | McFarland et al. ........ 73/24.06 |
| 6,336,353 B2 | * | 1/2002 | Matsiev et al. ............ 73/24.06 |
| 6,357,536 B1 | * | 3/2002 | Schrader et al. ............. 175/48 |
| 6,378,364 B1 | * | 4/2002 | Pelletier et al. .......... 73/152.47 |
| 6,393,895 B1 | * | 5/2002 | Matsiev et al. ............ 73/24.06 |
| 6,401,519 B1 | | 6/2002 | McFarland et al. |
| 6,494,079 B1 | | 12/2002 | Matsiev et al. |
| 2002/0088284 A1 | * | 7/2002 | Takeuchi et al. .............. 73/865 |

OTHER PUBLICATIONS

"Application of Low Frequency Mechanical Resonators to Liquid Property Measurments", L.F. Matsiev, J.W. Bennett & E.W. McFarland, 1998 IEEE Ultrasonics Symposium, pp. 459–462.

"Application of Flexural Mechanical Resonators to Simultaneous Measurments of Liquid Density and Viscosity", L.F. Matsiev, 1999 IEEE Ultrasonics Symposium, pp. 457–460.

"Application of Flexural Mechanical Resonators to High Throughput Liquid Characterization", L.F. Matsiev, 2000 IEEE International Ultrasonics Symposium, San Juan, Puerto Rico, Oct. 22–25, 2000.

Nangall Technology: www.nangall.com/products/plt/Fluid_Density_Tuned.htm (1989).

Nangall Technology: www.nangall.com/whatsnew.htm (Sep. 2001–Jun. 2003).

\* cited by examiner

METHOD AND APPARATUS FOR DOWNHOLE FLUID CHARACTERIZATION USING FLEXURAL MECHANICAL RESONATORS

CROSS REFERENCE TO RELATED APPLICATIONS

The patent application claims priority from U.S. patent application Ser. No. 60/291,136 filed on May 15, 2001 entitled "Method and Apparatus for Downhole Fluid Characterization Using Flexural Mechanical Resonators" by Rocco DiFoggio.

BACKGROUND OF THE INVENTION

1. Field of the Invention

The present invention relates to the field of downhole fluid analysis in hydrocarbon producing wells. More particularly, the present invention relates to a method and apparatus for determining fluid density, viscosity, and other parameters using a flexural mechanical resonator downhole in a borehole during monitoring while drilling or wire line operations.

2. Background of the Related Art

There is considerable interest in obtaining density and viscosity for formation fluids downhole at reservoir conditions of extreme temperature and pressure during formation sampling, production or drilling. Numerous technologies have been employed toward the end of measuring density and viscosity of liquids downhole. U.S. Pat. No. 6,182,499 discloses a system and method for characterization of materials and combinatorial libraries with mechanical oscillators. U.S. Pat. No. 5,734,098 discloses a method for monitoring and controlling chemical treatment of petroleum, petrochemical and processes with on-line quartz crystal microbalance sensors. The '098 method utilizes thickness shear mode (TSM) resonators, which simultaneously measure mass deposition and fluid properties such as viscosity and or density of a fluid. U.S. Pat. No. 6,176,323 discloses drilling systems with sensors for determining properties of drilling fluid downhole. The '323 patent discloses a plurality of pressure sensors at different depths to determine the fluid gradient.

U.S. Pat. No. 5,741,962 discloses a method and apparatus for analyzing a formation fluid using acoustic measurements. The '962 patent device acoustically determines density and compressibility from acoustic impedance and sound speed. U.S. Pat. No. 5,622,223 discloses a method and apparatus for formation fluid samples utilizing differential pressure measurements. The '223 patent discloses an apparatus that provides two pressure gauges at different depths to determine density from a fluid pressure gradient. U.S. Pat. No. 5,006,845 uses differential fluid pressure at two depths to determine fluid density. U.S. Pat. No. 5,361,632 discloses a method and apparatus for determining multiphase hold up fractions using a gradiometer and a densiometer to provide a pressure gradient to determine fluid density. U.S. Pat. No. 5,204,529 discloses a method and apparatus for measuring borehole fluid density, formation density and or borehole diameter using back-scattered gamma radiation to determine fluid density.

Flexural mechanical resonators have used in the laboratory has for rapid characterization of large numbers of fluid samples. See L. F. Matsiev, Application of Flexural Mechanical Resonator to High Throughput Liquid Characterization, 2000 IEEE International Ultrasonics Symposium, Oct. 22–25, 2000 San Juan, Puerto Rico, incorporated herein by reference in its entirety; L. F. Matsiev, Application of Flexural Mechanical Resonator to High Throughput Liquid Characterization, 1999 IEEE International Ultrasonics Symposium, October 17–20, Lake Tahoe, Nev., incorporated herein by reference in its entirety; L. F. Matsiev, Application of Flexural Mechanical Resonator to High Throughput Liquid Characterization, 1998 IEEE International Ultrasonics Symposium, Oct. 5–8, 1998, Sendai, Miyagi, Japan, incorporated herein by reference in its entirety.

There is, however, no method or apparatus for measuring viscosity in the downhole environment. Moreover, the inventor is aware of no known method or apparatus utilizing a flexural mechanical resonator to determine density, viscosity or other fluid properties in a downhole environment. Thus, there is a need for a method and apparatus utilizing a flexural mechanical resonator to determine density, viscosity or other fluid properties in a downhole environment.

SUMMARY OF THE INVENTION

The present invention provides a downhole method and apparatus using a mechanical resonator, for example, a tuning fork to provide real-time direct measurements and estimates of the viscosity, density and dielectric constant of formation fluid or filtrate in a hydrocarbon producing well. The present invention additionally provides a method and apparatus for 1) monitoring cleanup from a leveling off of viscosity or density over time, 2) measuring or estimating bubble point for formation fluid or filtrate, 3) measuring or estimating dew point for formation fluid or filtrate, and 4) the onset of asphaltene precipitation. The present invention also provides for intercalibration of a plurality of pressure gauges used to determine a pressure differential downhole. Each of these applications of the present invention contributes to the commercial value of downhole monitoring while drilling and wire line tools, such as the Baker Hughes/Baker Atlas Reservation Characterization Instrument (RCI). Thus, the present invention provides direct viscosity measurement capability that is currently unavailable in the oil services industry.

Known downhole tools can only measure the mobility or the ratio of permeability to viscosity. Thus, permeability and viscosity are not independently measured. The present invention enables the direct measurement of viscosity so that permeability can be determined from the measured mobility.

In one aspect of the invention, a downhole tool for determining the properties of a formation fluid sample is provided comprising a tool deployed in a well bore formed in an adjacent formation, the tool communicating and interacting with a quantity of downhole fluid, a mechanical resonator attached to the tool immersed in the fluid sample, a controller for actuating the mechanical resonator; and a monitor for receiving a response from the mechanical resonator to actuation of the mechanical resonator in the fluid. In another aspect of the invention a tool is provided further comprising a processor for determining a characteristic of a fluid sample from the response of the mechanical resonator. In another aspect of the invention a tool is provided wherein at least one of density, viscosity or dielectric constant are determined for a formation sample. In another aspect of the invention a tool is provided wherein the characteristic of said fluid is used to determine the dew point of said fluid. In another aspect of the invention a tool is provided wherein the characteristic of said fluid is used to determine the bubble point of a fluid sample. In another aspect of the invention a tool is provided where in the characteristic of the fluid is used to monitor the cleanup over time while pumping. In another aspect of the invention a tool is provided to determine the dew point of a down hole formation fluid sample. In another aspect of the invention a tool is provided wherein the characteristic of the fluid sample is used to determine the onset of asphaltene precipitation. In another aspect of the invention a tool is provided wherein the characteristic of the fluid sample is used to estimate NMR decay times T1 and T2, which are inversely correlated to viscosity. In another aspect of the invention a tool is provided further comprising a plurality of pressure gauges that are a known vertical separation distance apart in the fluid, wherein the mechanical resonator response is used to measure the density of the fluid to calculate the correct pressure difference for the amount of vertical separation. In another aspect of the invention, the mechanical resonator is actuated electrically. The resonator is made of quartz and has metallic electrodes deposited on two or more of the resonator faces. The electrodes are epoxy coated to prevent corrosion of the contacts. In another aspect of the invention, the mechanical resonator is placed in a cavity outside the direct flow path to protect the tuning fork from damage from debris passing in the sample flow path.

DETAILED DESCRIPTION OF A PREFERRED EMBODIMENT

Figure 1:
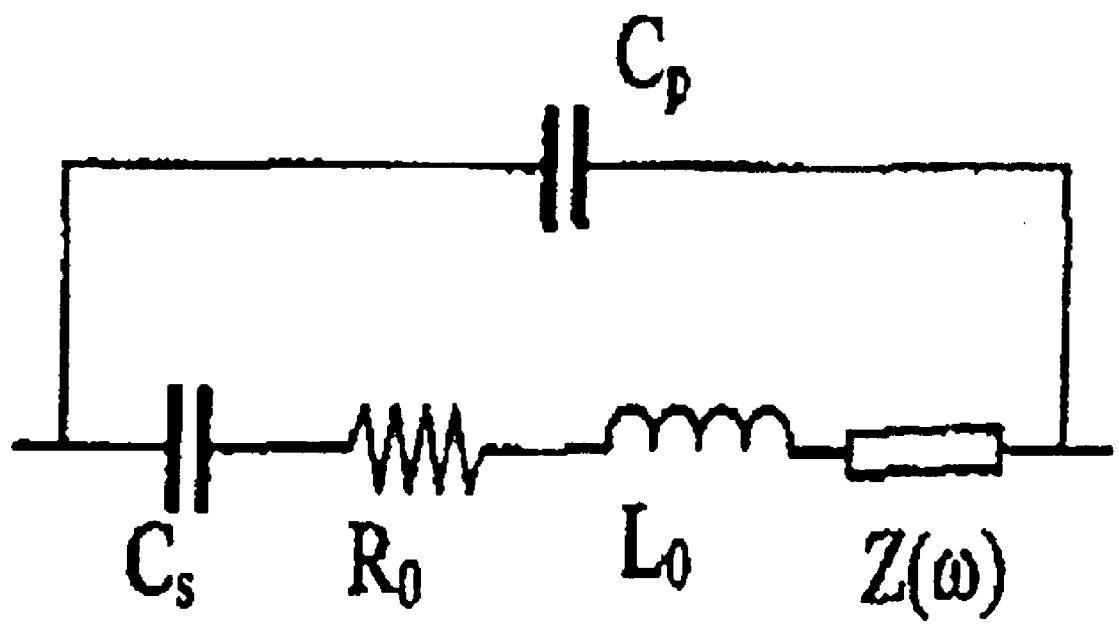
FIG. 1 is an illustration of a model for an equivalent circuit for a Thickness-shear mode (TSM) resonator complex impedance in a liquid environment.

The inventors are aware of no method or apparatus for directly measuring density, viscosity or dielectric constant downhole using a flexural mechanical resonator. The present invention provides a downhole method and apparatus using a mechanical resonator, preferably, a tuning fork to provide real-time direct measurements and estimates of the viscosity, density and dielectric constant for formation fluid or filtrate in a hydrocarbon producing well. The present invention additionally provides a method and apparatus for: 1) monitoring cleanup from a leveling off of viscosity or density over time as the fluid under investigation transitions from contaminated to substantially pure formation fluid; 2) measuring or estimating bubble point for formation fluid; 3) measuring or estimating dew point for formation fluid; and 4) the onset of asphaltene precipitation. Each of these applications contribute to the commercial value of downhole monitoring while drilling and wire line tools, such as the Baker Hughes/Baker Atlas Reservation Characterization Instrument.

There currently is no method or apparatus for directly measuring viscosity in the down hole environment, thus, the present invention provides measurement capability that is currently unavailable in the oil services industry.

The Matsiev reference describes the application of flexural mechanical resonators such as tuning forks, benders, etc. to liquid characterization. Additional complex electrical impedance produced by a liquid environment to such resonators is also described. Matsiev shows that this additional impedance can be represented by the sum of two terms: one that is proportional to liquid density and a second one that is proportional to the square root the of viscosity density product. This impedance model is universally applicable to any resonator type that directly displaces liquid and has size much smaller than the acoustic wavelength in a liquid at its operation frequency. Using this model it is possible to separately extract liquid viscosity and density values from the flexural resonator frequency response, while conventional TSM resonators can measure only the viscosity density product.

Thickness-shear mode (TSM) quartz resonators have been applied to the determination of mechanical properties of liquids for several decades. Oscillation of the TSM resonator surface exposed to liquid along a crystal-liquid interface produces a decaying viscous shear wave in liquid. A simple relationship between the impedance of the TSM resonator change caused by contact with a liquid and the viscosity density product of liquid has been derived using a simple one-dimensional mathematical model and is supported experimentally. It was found that the TSM resonator complex impedance in a liquid environment could be represented by equivalent circuit shown on FIG. 1.

Equivalent parameters $C_s$, $R_o$, $L_0$ represent respectively mechanical compliance, loss and inertia of the resonator in vacuum. Additional impedance $Z(\omega)$ produced by surrounding liquid is given by $(\omega\rho\eta)^{1/2}(1+i)$ per unit interface area, where $\omega$ is the operation frequency, $\rho$ is the liquid density, $\eta$ is the viscosity of the liquid. Parallel capacitance $C_\eta$, an electrical capacitance measured between the resonator electrodes, is also affected by electrical properties of surrounding liquid.

TSM quartz resonators have been successfully used for characterization of liquids. Unfortunately, quartz TSM resonators suffer from several serious drawbacks: 1) It is necessary to make additional experiments to measure liquid density and viscosity separately; and 2) viscosity and other properties of even low molecular weight liquids depend on frequency. The operation frequency of commercially available TSM resonators usually ranges from one to several tens of megahertz so TSM resonators measure the high-frequency response the fluid.

In practice, low-frequency response is usually more interesting. For example, most lubricants work under low-frequency shear stress. In the case of polymer solutions, TSM resonator response is virtually independent of polymer molecular weight and depends only on polymer concentration. All relaxation times from the polymer chain relaxation spectrum are usually much longer than the circle of viscous stress applied by TSM resonator, so the TSM resonator reacts as if it were in a solution of "solid" coils; almost all types of molecular motion seem frozen.

To avoid such problems low-frequency piezoelectric resonators such as bar benders, disk benders, cantilevers, tuning forks, micro-machined membrane and torsion resonators can be used. A wide variety of such resonators with operation frequency from hundreds of hertz up to few MHz are commercially available.

Figure 2:
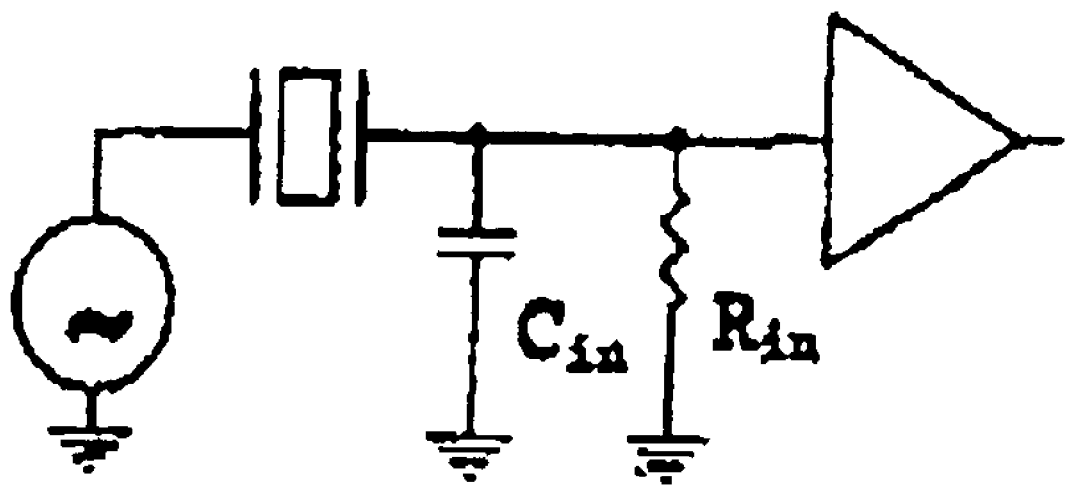
FIG. 2 is an illustration of resonator connections in a preferred embodiment.

There are a variety of ways to measure resonator response in a liquid environment. Matsiev used an HP8751A network analyzer to sweep frequencies and measure response when the resonator was exposed to a variety of organic solvents. The equivalent impedance of tuning forks is quite high, so the use of high impedance probe is recommended. In a preferred embodiment an exciter circuit is provide and the resonator is connected as shown on FIG. 2.

Figure 3A:
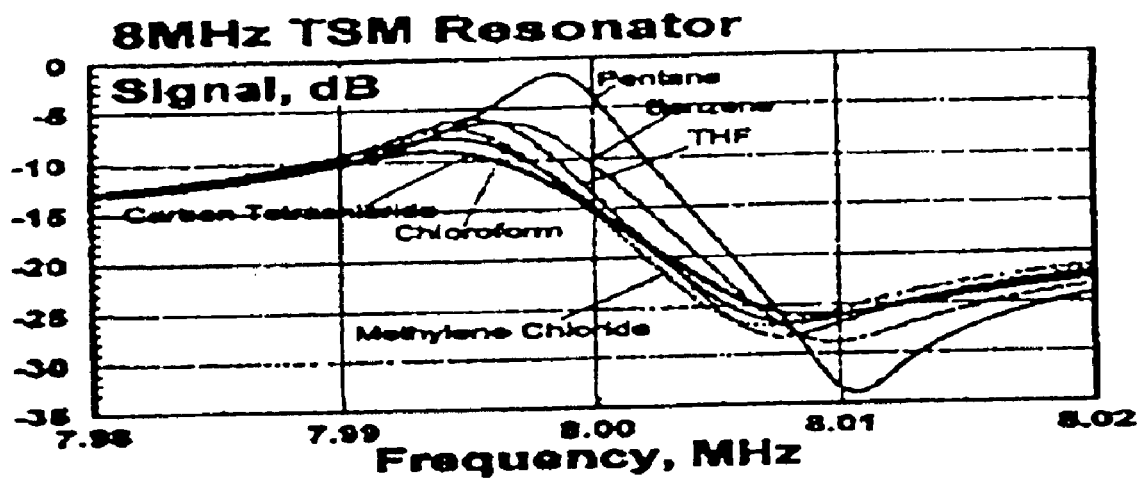
FIG. 3A is an illustration of typical frequency response of a conventional TSM resonator in various solvents.
Figure 3B:
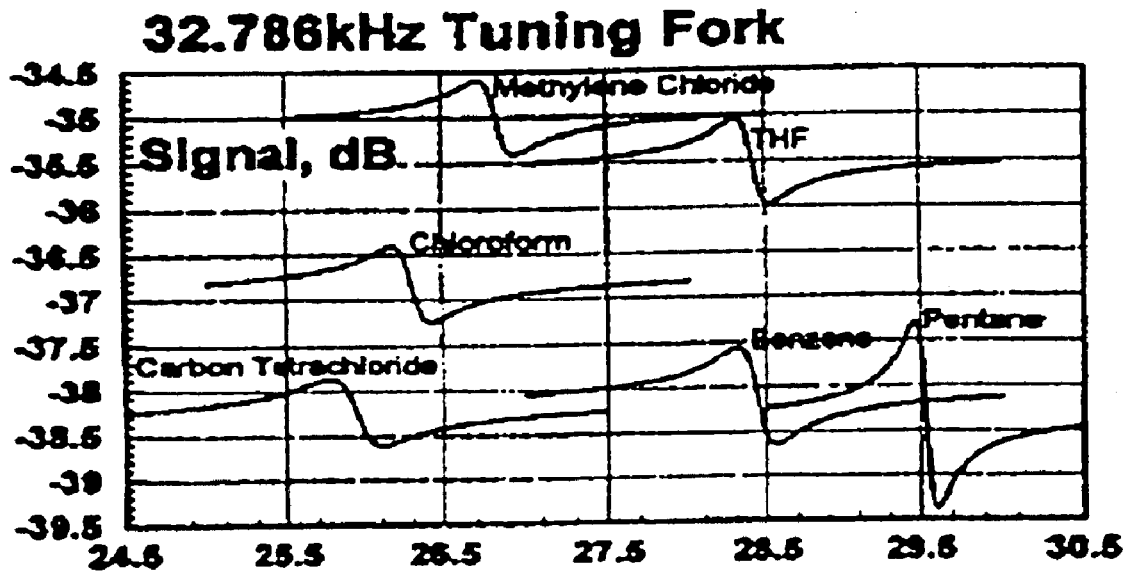
FIG. 3B is an illustration of typical frequency response of a tuning fork in various solvents.

The resonator impedance and probe amplifier known input impedance form frequency dependent voltage divider. The frequency dependence of the normalized absolute value of the probe input voltage was recorded while resonator was submerged in various organic solvents. Typical frequency responses of conventional 8 MHz TSM resonator and 32.768 kHz tuning fork in various solvents are shown on FIGS. 3A and 3B respectively.

It is evident that the response of a tuning fork resonator is more strongly affected by the properties of the liquid than the response of a TSM resonator. Thus the tuning fork resonator thus provides much better resolution in the determination of liquid properties.

The equivalent circuit from FIG. 1 also describes the impedance of the flexural resonator with a modification for the additional impedance $Z(\omega)$. Despite the complexity of such a 3D problem it is possible to state that the flow is in effect a viscous flow of an incompressible liquid. Oscillation velocity at the interfaces of an oscillating flexural resonator does have a component normal to the interface, so some compression should occur. At the same time, the size of flexural resonators is much less than a wavelength of the compression wave in surrounding liquid at operational frequency. Therefore low-frequency resonators are, in general, quite ineffective exciters of compression waves regardless of the oscillation mode.

For viscous incompressible flow the vorticity of the velocity field decays with the distance from the oscillating body in the same manner as the velocity decays with the distance from TSM resonator. This means that some component of the additional impedance of a flexural resonator should be proportional to $(\omega\rho\eta)^{1/2}(1+i)$ as is the case for the TSM resonator, with some unknown coefficient or geometry factor, which itself depends upon the resonator geometry and oscillation mode.

In contrast to TSM resonators flexural resonators directly displace liquid. The virtual hydrodynamic mass attached to a body moving in a liquid due to direct displacement depends only on the body geometry and liquid density. It should manifest itself as an additional inductive component of the equivalent impedance proportional to liquid density.

That additional impedance of a flexural resonator is represented by the following relationship: $Z(\omega)=Ai\omega\rho+B\sqrt{\omega\rho\eta}(1+i)$, where $\omega$ is the operation frequency, $\rho$ is the liquid density, $\eta$ is the liquid viscosity, A and B are the geometry factors that depend only on the resonator geometry and mode of oscillation. Alternatively, this relationship can be rewritten as: $Z(\omega)=i\omega\Delta L+\Delta Z\sqrt{\omega}(1+i)$, where $\Delta L=A\rho$ and $\Delta Z=B\sqrt{\rho\eta}$ are frequency independent parameters, which can be easily calculated by fitting experimental data using, for example, the least squares method.

Figure 4A:
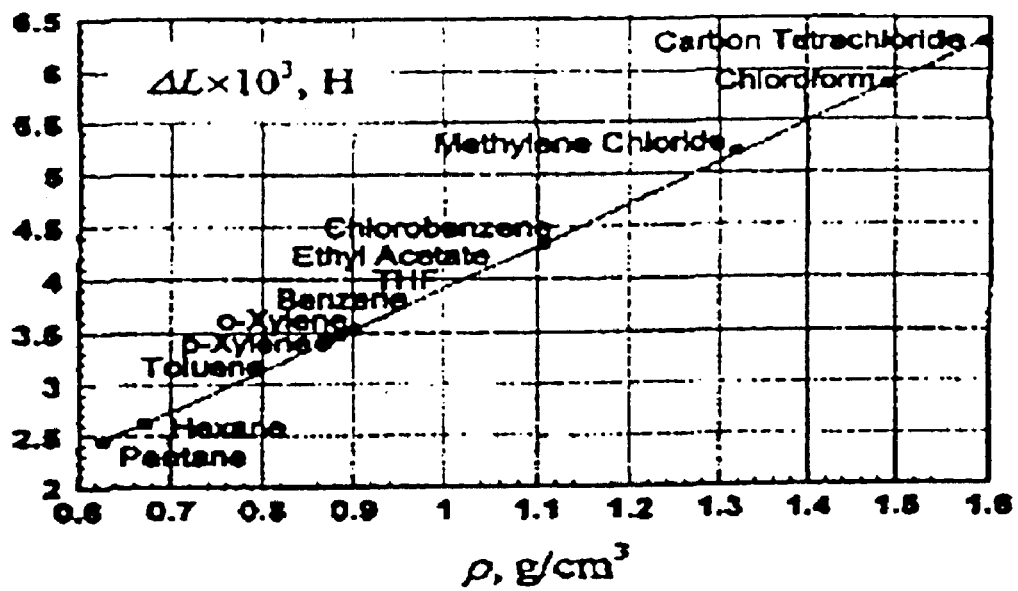
FIG. 4A is an illustration of values for delta $\Delta L$ plotted versus solvent density and square root of the solvent viscosity density product.
Figure 4B:
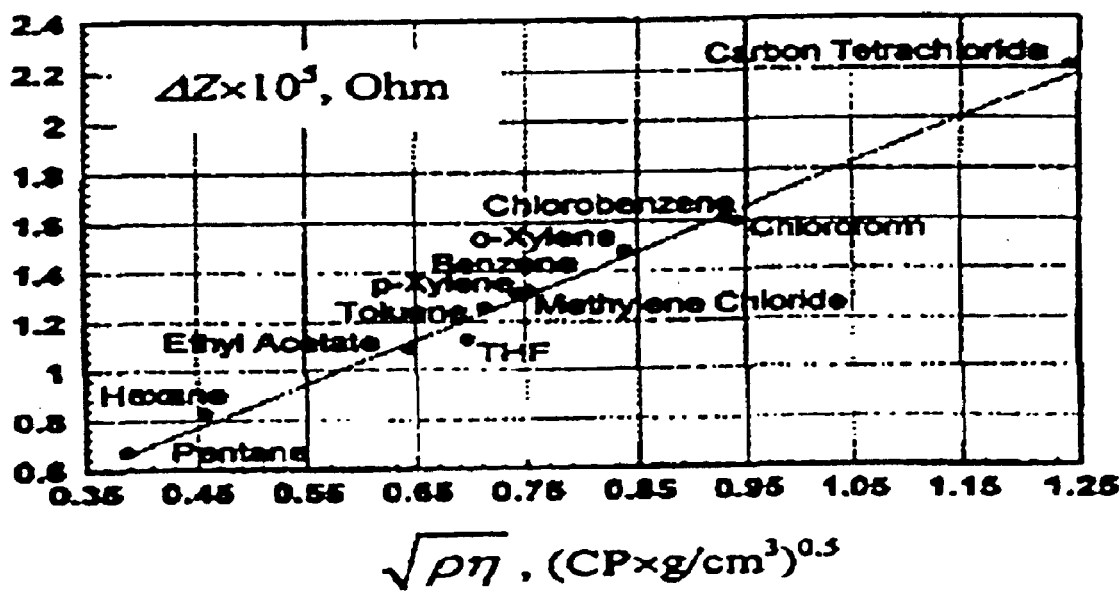
FIG. 4B is an illustration of values for $\Delta Z$ plotted versus solvent density and square root of the solvent viscosity density product.

Acquired data on the frequency response of the 32.768 kHz tuning fork resonator for a variety of common organic solvents generating a family of curves, are shown in FIG. 3. Values for $\Delta L$ and $\Delta Z$ were determined by fitting the frequency response data to the proposed mathematical model. In general the model was found to be in excellent agreement with the data; the residuals could be entirely attributed to electronic noise rather than the difference between the model and the data. Values for $\Delta L$ and $\Delta Z$ plotted versus the solvent density and square root of the solvent viscosity density product, respectively, are shown in FIG. 4. Density and viscosity values were taken from literature (CRC, Aldrich). The standard deviation for ordinate values on both plots calculated by fitting software is less than the size of the data point marker.

In practice, low-frequency response is usually more interesting. For example, most lubricants work under low-frequency shear stress. In the case of polymer solutions, TSM resonator response is virtually independent of polymer molecular weight and depends only on polymer concentration. All relaxation times from the polymer chain relaxation spectrum are usually much longer than the circle of viscous stress applied by TSM resonator, so the TSM resonator reacts as if it were in a solution of "solid" coils; almost all types of molecular motion seem frozen.

To avoid such problems low-frequency piezoelectric resonators such as bar benders, disk benders, cantilevers, tuning forks, micro-machined membrane and torsion resonators can be used. A wide variety of such resonators with operation frequency from hundreds of hertz up to few MHz are commercially available.

TSM resonators do not move fluid substantially and thus do not separately yield density and viscosity of a fluid. Flexural mechanical resonators respond to the both the density and viscosity of a fluid into which they are immersed. Symyx Technologies Incorporated of Santa Clara, Calif. has developed a model for a miniature tuning fork resonator, which enables separate determination of density and viscosity of fluid, rather than merely the product of these two properties as described in the three papers authored by Matsiev of Symvx discussed above. TSM resonators can only determine the product of density and viscosity and thus viscosity or density could not be independently determined. The present invention provides a tuning fork or flexural resonator, which is excited, monitored and process to separately determine not only the density and viscosity of a fluid, but also the dielectric constant of a fluid. The preferred resonator tuning forks are very small, approximately 2 mm×5 mm, are inexpensive and have no macroscopically moving parts. The resonator tuning forks can operate at elevated temperature and pressure and enable a more accurate method of determining viscosity and other fluid properties downhole than other known methods. The tuning forks are provided by Symyx and are made of quartz with silver or gold electrodes. Symyx states that the typical accuracy for determination is ±0.01% for density, ±1.0% for viscosity, and ±0.02% for dielectric constant. In a preferred embodiment, the electrodes are connected to wires. The connections between the wires and electrodes are covered with epoxy to prevent corrosion of the connections to the electrodes.

The most common method for determining downhole fluid density is determination of the pressure gradient. Density is proportional to the slope of a plot of pressure versus depth over a depth interval of 50–150 feet. Generally, the tool is moved from point to point in the well so that the same pressure gauge is used to make all the pressure readings. It is hard to keep two different pressure gauges inter-calibrated within a few tenths of a PSI at high temperatures and pressures.

U.S. Pat. No. 5,622,223 discloses the use of differential pressure gauges spaced closely together so that to fit within the length of a tool and thus does not require relocation of the tool to make a pressure gradient measurement. It is not clear how the two pressure gauges are inter-calibrated. Inter-calibration could be attempted utilizing the known density of the drilling mud and its pressure gradient as the calibrator. A density measurement can also be made from the acoustic reflection intensity at the interface of an unknown fluid and a known solid as disclosed in U.S. Pat. No. 5,741,962. Density can also be measured using gamma rays as disclosed in U.S. Pat. No. 5,204,529.

The measurement of viscosity downhole can be estimated form the well-known inverse relationship between Nuclear Magnetic Resonance (NMR) decay time and viscosity. Alternatively, any differential pressure gauge sensitive enough to determine density from a short-spacing (10–20 feet) pressure gradient should be sufficiently sensitive to determine viscosity from the pressure drop versus flow rate in a wire line formation tester. The present invention enables making an accurate differential pressure gauge based on the present invention enabling performing inter-calibration between two pressure gauges.

The flexural mechanical oscillator generates a signal which is utilized to determine formation fluid properties and transmits the signal to a processor or intelligent completion system (ICE) 30 for receiving, storing and processing the signal or combination of signals.

Figure 5:
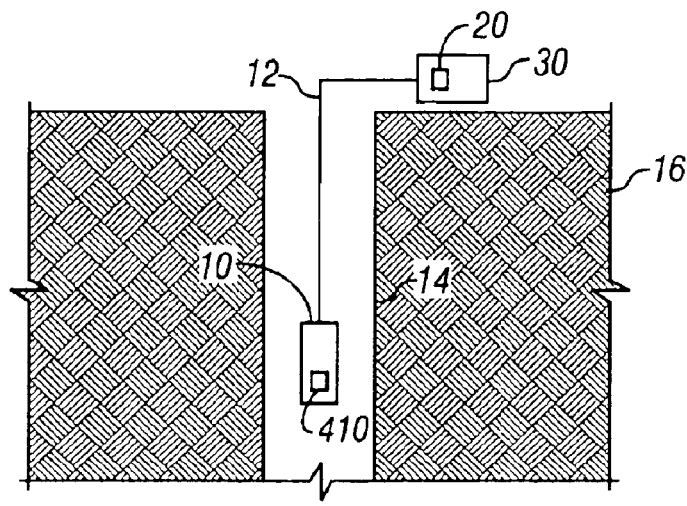
FIG. 5 is a schematic diagram of a preferred embodiment of the present invention deployed on a wire line in a downhole environment.
Figure 6:
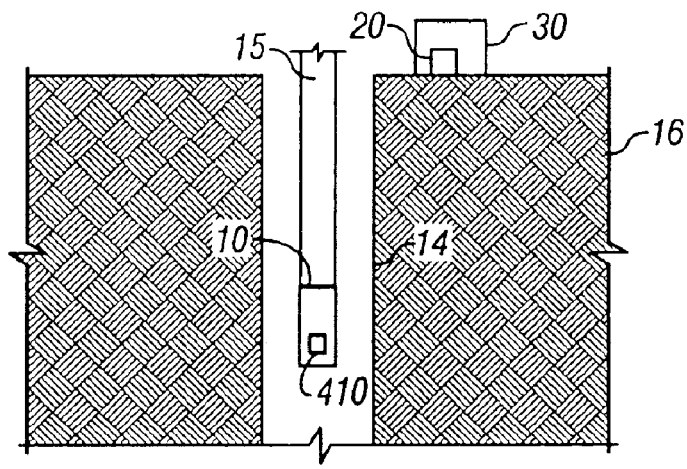
FIG. 6 is a schematic diagram of a preferred embodiment of the present invention deployed on a drill string in a monitoring while drilling environment.
Figure 7:
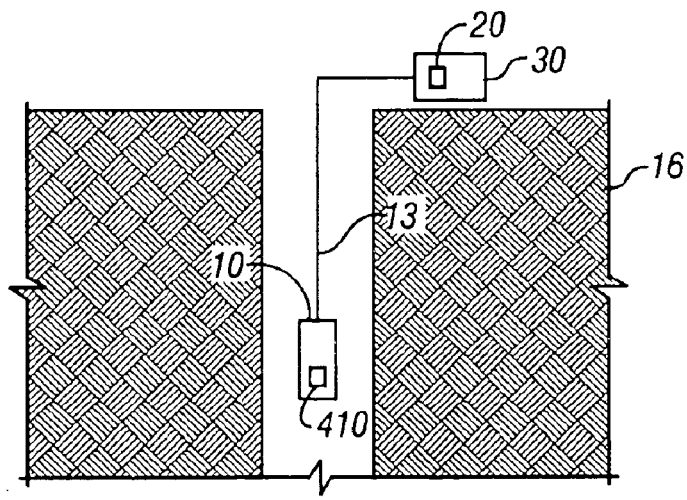
FIG. 7 is a schematic diagram of a preferred embodiment of the present invention deployed on a flexible tubing in a downhole environment.

FIG. 5 is a schematic diagram of a preferred embodiment of the present invention deployed on a wire line in a downhole environment. As shown in FIG. 5, a downhole tool 10 containing a mechanical resonator 410 is deployed in a borehole 14. The borehole is formed in formation 16. Tool 10 is deployed via a wireline 12. Data from the tool 10 is communicated to the surface to a computer processor 20 with memory inside of an intelligent completion system 30. FIG. 6 is a schematic diagram of a preferred embodiment of the present invention deployed on a drill string 15 in a monitoring while drilling environment. FIG. 7 is a schematic diagram of a preferred embodiment of the present invention deployed on a flexible tubing 13 in a downhole environment.

Figure 8:
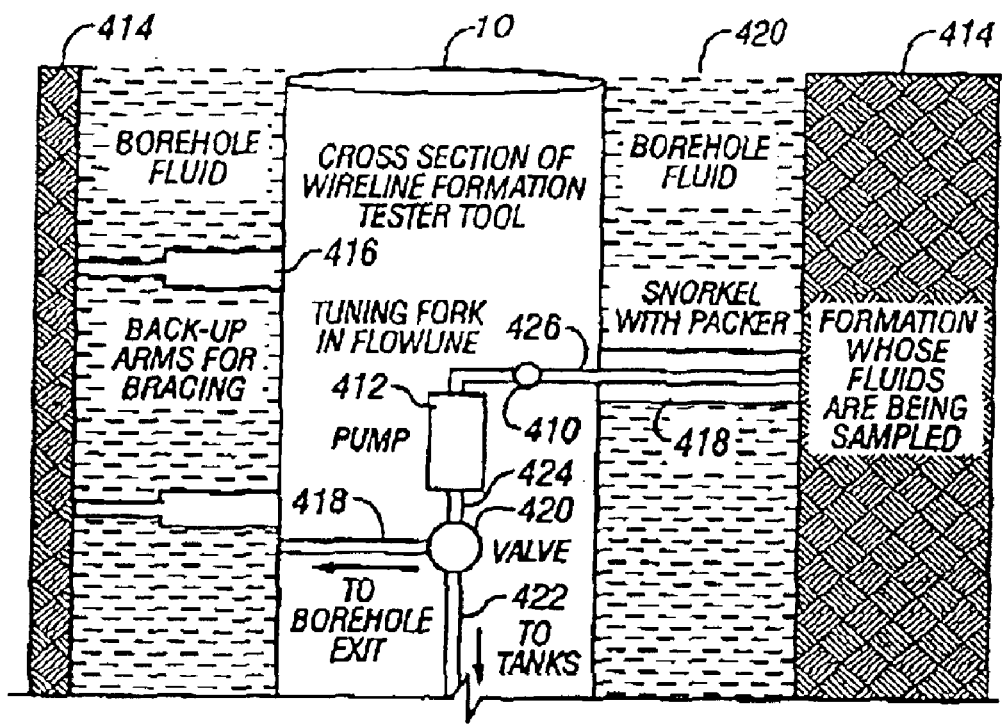
FIG. 8 is a schematic diagram of a preferred embodiment of the present invention as deployed in a wireline downhole environment showing a cross section of a wireline formation tester tool.

FIG. 8 is a schematic diagram of a preferred embodiment of the present invention as deployed in a wireline downhole environment showing a cross section of a wireline formation tester tool. As Shown in FIG. 8, tool 10 is deployed in a borehole 420 filled with borehole fluid. The tool 10 is positioned in the borehole by backup support arms 416. A packer with a snorkel 418 contacts the borehole wall for extracting formation fluid from the formation 414. Tool 10 contains tuning fork 410 disposed in flowline 426. Any type of flexural mechanical oscillator is suitable for deployment in the tool of the present invention. The mechanical oscillator, shown in FIG. 8 as a tuning fork is excited by a electric current applied to its electrodes and monitored to determine density, viscosity and dielectric coeficient of the formation fluid. The electronics for exciting and monitoring the flexural mechanical resonator as shown in the Matsiev references are housed in the tool 10. Pump 412 pumps formation fluid from formation 414 into flowline 426. Formation fluid travels through flow line 424 in into valve 420 which directs the formation fluid to line 422 to save the fluid in sample tanks or to line 418 where the formation fluid exits to the borehole. The tuning fork is excited and its response in the presence of a formation fluid sample is utilized to determine fluid density, viscosity and dielectric coefficient while fluid is pumped by pump 412 or while the fluid is static, that is, when pump 412 is stopped.

Figure 9A:
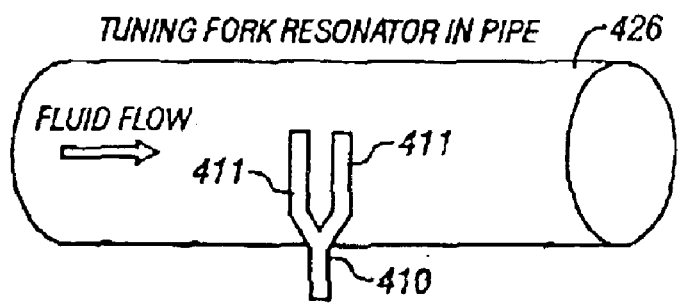
FIG. 9A is a schematic diagram of a preferred embodiment of the present invention illustrating a tuning fork as deployed in a fluid flow pipe.
Figure 9B:
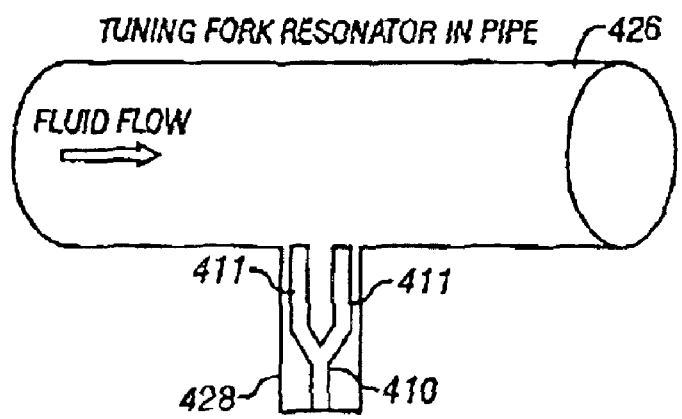
FIG. 9B is a schematic diagram of an alternative embodiment of the present invention illustrating a tuning fork as deployed in a recess formed in fluid flow pipe to remove the tuning fork from the majority of the turbulence of the fluid flowing in the flow path but still in contact with the fluid flowing in the flow pipe.

FIG. 9A is a schematic diagram of a preferred embodiment of the present invention illustrating a tuning fork 410 with tines 411 deployed in a fluid flow pipe 426. FIG. 9B is an alternative embodiment of the present invention in which the turning fork is recessed out of the flow pipe into a recess, cavity or clean out 428. The location of the tuning fork in the recess, out of the flow pipe in the recess helps prevent abrasion or damage to the tuning fork from turbulence or sand and other debris present in the formation fluid sample as the formation fluid flows in the flow pipe.

Figure 10:
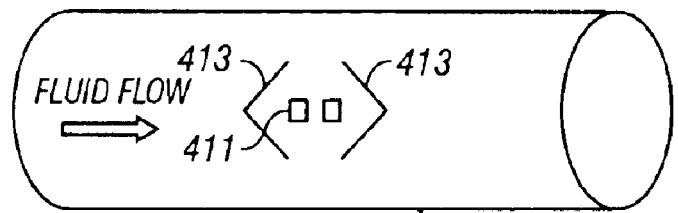
FIG. 10 is a schematic diagram of a preferred embodiment of the present invention showing protection baffles.
Figure 11:
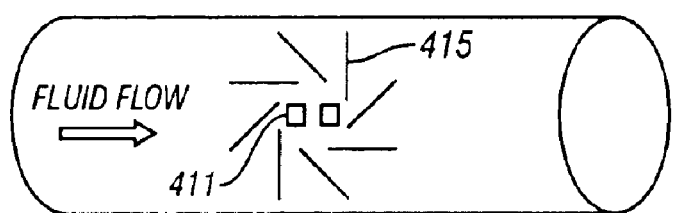
FIG. 11 is a schematic diagram of an alternative embodiment of the present invention showing an alternative embodiment of the protection baffles surrounding mechanical resonator.
Figure 12:
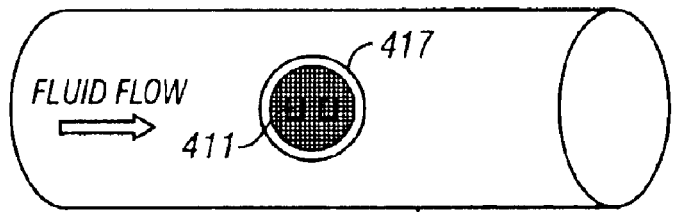
FIG. 12 is a schematic diagram of an alternative embodiment of the present invention showing a sintered metal cap or screen protecting mechanical resonator.

FIG. 10 is a schematic diagram of a preferred embodiment of the present invention showing protection baffles 413 surrounding tuning fork tines 411 inside of flow pipe 426. FIG. 11 is a schematic diagram of an alternative embodiment of the present invention showing an alternative embodiment of the protection baffles 415 surrounding mechanical resonator tuning fork tines 411 inside of flow pipe 426. FIG. 12 is a schematic diagram of an alternative embodiment of the present invention showing a sintered metal cap 417 protecting mechanical resonator, tuning fork tines 411 inside of fluid flow pipe 426. Sintered metal caps are available from Mott Corporation, 84 Spring Lane, Farmington, Conn. 06032.

Figure 13:
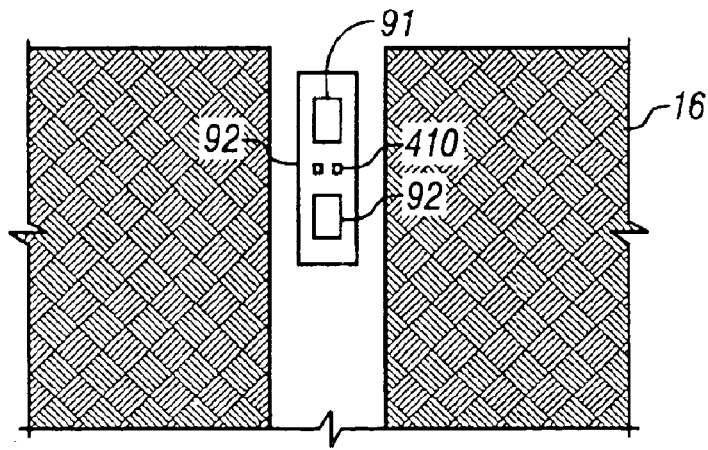
FIG. 13 is a schematic of the preferred embodiment showing two pressure gauges for intercalibration.

Turning now to FIG. 13, FIG. 13 is a schematic diagram of a two pressure gauges 91 and 92 provided in a down hole tool having a mechanical resonator 410, in this case a tuning form 410 for inter-calibration between pressure gauges 91 and 92.

As shown in FIG. 8, the present invention can be utilized in flowing fluid, as when a sample of well bore fluid or formation fluid is pumped through the tool and into the well bore. In this scenario, where fluid is pumped through the tool, the mechanical resonator, which can be a bar bender, disk bender, cantilever, tuning fork, micro-machined membrane or torsion resonator, is immersed in the flowing fluid and used to determine the density, viscosity and dielectric constant for the fluid flowing in the tool. In a preferred embodiment, baffles are provided in the flow path to protect the mechanical resonator from the physical stress of the flowing fluid. A porous, sintered metal cap or a screen can also be used to cover the mechanical oscillator and protect it from pressure pulses and particles of sand or other solids. As shown in FIG. 9B, in an alternative embodiment, the tuning fork is placed out of the flow path in a recess 428 to protect the tuning fork from harm from the turbulence and debris associated with the fluid sample flowing in the flow pipe.

In a second scenario of operation the fluid sample flowing in the tool is stopped from flowing by stopping the pump 412 while the mechanical resonator is immersed in the fluid and used to determine the density, viscosity and dielectric constant for the static fluid trapped in the tool.

Samples are taken from the formation by pumping fluid from the formation into a sample cell. Filtrate from the borehole normally invades the formation and consequently is typically present in formation fluid when a sample is drawn from the formation. As formation fluid is pumped from the formation the amount of filtrate in the fluid pumped from the formation diminishes over time until the sample reaches its lowest level of contamination. This process of pumping to remove sample contamination is referred to as sample clean up. In a preferred embodiment, the present invention indicates that a formation fluid sample clean up is complete when the viscosity or density has leveled off or become asymptotic within the resolution of the measurement of the tool for a period of twenty minutes to one hour. A density or viscosity measurement is also compared to a historical measure of viscosity or density for a particular formation and or depth in determining when a sample is cleaned up. That is, when a sample reaches a particular level or value for density and or viscosity in accordance with a historical value for viscosity and or density for the formation and depth the sample is determined to have been cleaned up to have reached a desired level of purity.

The bubble point pressure for a sample is indicated by that pressure at which the measured viscosity for formation fluid sample decreases abruptly. The dew point is indicated by an abrupt increase in viscosity of a formation fluid sample in a gaseous state. The asphaltene precipitation pressure is that pressure at which the viscosity decreases abruptly.

The present invention also enables calibration of a plurality of pressure gauges at depth. Pressure gauges are typically very sensitive to changes but not accurate as to absolute pressure. That is, a pressure gauge can accurately determine a change of 0.1 PSI but not capable of accurately determining whether the pressure changed from 1000.0 to 1000.1 PSI or 1002.0 to 1002.1 PSI. That is, the precision is better than the accuracy in the pressure gauges. In a preferred embodiment, the present invention enables determination of the absolute pressure difference between pressure gauges in a downhole tool. The present invention enables determination of die density of the fluid. Since the distance between the downhole pressure gauges is known, one can determine what the pressure difference or offset should be between the pressure gauges at a particular pressure and temperature. This calibration value or offset is added to or subtracted from the two pressure gauge readings. The calibration value is calculated in a nonconductive fluid, such as oil and can be applied when measuring pressure differential in conductive fluid, such as water where the tuning fork will not measure density or in the non-conductive fluid.

In a preferred embodiment, the dielectric constant is calculated for a formation fluid sample as discussed in the Matsiev references. The present invention utilizes the Matsiev calculations to calculate density and viscosity. The present invention provides a chemometric equation derived from a training set of known properties to estimate formation fluid parameters. The present invention provides a neural network derived from a training set of known properties to estimate formation fluid parameters. For example, from a measured viscosity, a chemometric equation can be used to estimate NMR properties $T_1$ and $T_2$ for a sample to improve an NMR measurement made independently in the tool. The chemometric equation is derived from a training set of samples for which the viscosity and NMR $T_1$ and $T_2$ are known. Any soft modeling technique is applicable with the present invention.

The present invention is utilized to provide density, viscosity, dielectric coefficient and other measured or derived information available from the tool of the present invention to a processor or intelligent completion system (ICS) at the surface. The ICS is a system for the remote, interventionless actuation of downhole completion equipment has been developed to support the ongoing need for operators to lower costs and increase or preserve the value of the reservoir. Such a system is described in The Oil and Gas Journal, Oct. 14, 1996.

These needs are particularly important in offshore environments where well intervention costs are significantly higher than those performed onshore, For example, traditional methods for setting a production packer employ coiled tubing or slick line to run a tubing plug. The new system provides a safe, reliable and more cost efficient alternative to this method because it simply transmits acoustic pulses through the contents of tubulars to actuate one or more completion or service tools remotely i any desired sequence. The system not only decreses the sampling time and the time the packer is set, and also extends the envelope for application to deep, extended-reach offshore environments. Since the system eliminates the need to circulate a ball downhole to set service tools during sand control operations, the operator can maintain constant hydrostatic pressure on the formation. This capability decreses competion time, intervention risk, the possibility of fromation collapse against the competion string, the possibility of losing the filter cake placed against the formation, and fluid loss to the formation. To achieve the goals required for this system, three project targets were addressed: a reliable means of wireless communication, a surface control system, and a downhole power unit for completion device actuation. The design and capabilities of the new surface-operated, non-intervention completion system will facilitate economic completions in situations where more complex systems could not be justified, thus increasing the scope of application for 'intelligent well' technology.

At times called "SmartWells," these completion systems enable oil and gas companies to study and control individual zones without well intervention. This can dramatically lower operating expenditures by reducing downtime. Also, it can allow enhanced hydrocarbon recovery via improved reservoir management. ICSs enable the operator to produce, monitor and control the production of hydrocarbons through remotely operated completion systems. These systems are developed with techniques that allow the well architecture to be reconfigured at will and real-time data to be acquired without any well intervention.

The operator, located at the surface and having access to over ride the processor/ICE 30 may make his own decisions and issue commands concerning well completion based on the measurements provided by the present invention. The present invention may also provide data during production logging to determine the nature of fluid coming through a perforation in the well bore, for example, the water and oil ratio.

The foregoing example is for purposes of example only and is not intended to limit the scope of the invention which is defined by the following claims.

What is claimed is:

1. A downhole tool for determining a property of a fluid comprising:
   a flexural piezoelectric resonator in the fluid for displacing the fluid;
   a controller for actuating the flexural piezoelectric resonator;
   a monitor which measures an electrical impedance versus frequency from the flexural piezoelectric resonator; and
   at least one of the set consisting of a recess, sintered metal cap and baffles associated with the downhole tool for protecting the flexural piezoelectric resonator.

2. A method for estimating a property of a downhole fluid comprising:
   disposing a flexural piezoelectric resonator in the downhole fluid;
   directly moving the downhole fluid by actuating the flexural piezoelectric resonator;
   measuring an electrical impedance versus frequency of the flexural piezoelectric resonator;
   estimating a property of the downhole fluid from the measured electrical impedance; and
   disposing the flexural piezoelectric resonator in a recess out of a flow path for the formation sample.

3. A method for estimating a property of a downhole fluid comprising:
   disposing a flexural piezoelectric resonator in the downhole fluid;
   directly moving the downhole fluid by actuating the flexural piezoelectric resonator;
   measuring an electrical impedance versus frequent of the flexural piezoelectric resonator;
   estimating a viscosity of the downhole fluid from the measured electrical impedance; and
   indicating a dew point pressure for the downhole fluid from an abrupt increase in the viscosity.

4. A method for estimating a property of a downhole fluid comprising:
   disposing a flexural piezoelectric resonator in the downhole fluid;
   directly moving the downhole fluid by actuating the flexural piezoelectric resonator;
   measuring an electrical impedance versus frequency of the flexural piezoelectric resonator;
   estimating a viscosity of the downhole fluid from the measured electrical impedance; and
   indicating bubble point pressure for the downhole fluid from an abrupt decrease in the viscosity.

5. A method for estimating a property of a downhole fluid comprising:
   disposing a flexural piezoelectric resonator in the downhole fluid;
   directly moving the downhole fluid by actuating the flexural piezoelectric resonator;
   measuring an electrical impedance versus frequency of the flexural piezoelectric resonator;
   estimating a property of the downhole fluid from the measured electrical impedance; and
   determining when the property of the downhole fluid has leveled off to indicate that the fluid has been cleaned up.

6. A method for estimating a property of a downhole fluid comprising:
   disposing a flexural piezoelectric resonator in the downhole fluid;
   directly moving the downhole fluid by actuating the flexural piezoelectric resonator;
   measuring an electrical impedance versus frequency of the flexural piezoelectric resonator;
   estimating a viscosity of the downhole fluid from the measured electrical impedance; and
   indicating the onset of asphaltene precipitation by an abrupt decrease in viscosity.

7. A downhole tool for determining a property of a fluid comprising:
   a flexural piezoelectric resonator in the sample of fluid for displacing the fluid;
   a controller for actuating the flexural piezoelectric resonator;
   a monitor which measures an electrical impedance versus frequency from the flexural piezoelechic resonator; and
   two pressure gauges which measure pressures to estimate density of the fluid.

8. A method for estimating a property of a downhole fluid comprising:
   disposing a flexural piezoelectric resonator in the downhole fluid;
   directly moving the downhole fluid by actuating the flexural piezoelectric resonator;
   measuring an electrical impedance versus frequency of the flexural piezoelectric resonator;
   estimating density of the downhole fluid from the measured electrical impedance versus frequency; and
   inter-calibrating two pressure gauges at a pressure and temperature down hole based on the density of the fluid and a distance between the gauges.

9. The method of claim 8, further comprising:
   using the intercalibrated pressure gauges to measure the density of conductive downhole fluid.

10. The method of claim 8, further comprising:
    using the intercalibrated pressure gauges to measure the density of a downhole fluid that cannot be measured directly with the flexural piezoelectric resonator.

11. The method of claim 8, further comprising:
    using pressure gauges to estimate viscosity of the downhole fluids from a flow rate and pressure drop between the pressure gauges.

12. An apparatus for estimating a property of a downhole fluid comprising:
    a flexural piezoelectric resonator disposed in the downhole fluid;
    a controller that actuates the flexural piezoelectric resonator at a frequency;
    a monitor that measures electrical impedance versus the frequency of the flexural piezoelectric resonator; and
    a processor that estimates the property of the downhole fluid from the measured electrical impedance.

13. The apparatus of claim 12, wherein the frequency is a swept frequency and the processor estimates the property of the downhole fluid from the measured electrical impedance versus the swept frequency.

14. The apparatus of claim 12, wherein the property of the downhole fluid comprises at least one of the set consisting of density, viscosity, permeability and dielectric constant.

15. The apparatus of claim 12, wherein the processor uses the property of the downhole fluid and at least one of the set consisting of a chemometric equation and a neural network to estimate a secondary property of the downhole fluid.

16. The apparatus of claim 15, wherein the secondary property of the downhole fluid comprises nuclear magnetic resonance relaxation time.

17. The apparatus of claim 12, wherein the flexural piezoelectric resonator comprises at least one of the set consisting of a bar bender, disk bender, cantilever, a tuning fork, micro-machined membrane and torsion resonator.

18. The apparatus of claim 12, wherein the flexural piezoelectric resonator has a dimension smaller than an acoustic wavelength of the actuating frequency.

19. A method for estimating a property of a downhole fluid comprising:
 disposing a flexural piezoelectric resonator in the downhole fluid;
 directly moving the fluid by actuating the flexural piezoelectric resonator;
 measuring an electrical impedance versus frequency of the flexural piezoelectric resonator; and
 estimating the property of the downhole fluid from the measured electrical impedance.

20. The method of claim 19, wherein the flexural piezoelectric resonator is actuated at a swept frequency, the method further comprising:
 estimating the property of the downhole fluid from the measured electrical impedance versus the swept actuating frequency.

21. The method of claim 19, wherein the property of the downhole fluid comprises at least one of the set consisting of density, viscosity, dielectric constant and permeability.

22. The method of claim 19, further comprising:
 estimating viscosity of the downhole fluid in a flow line from a flow rate in the flow line and a pressure decrease between two points on the flow line using pressure measurements from the inter-calibrated pressure gauges 23. The method of claim 19, further comprising:
 estimating another property of the downhole fluid from the property and at least one of the set consisting of a neural network and chemometric equation.

24. A downhole tool for estimating a property of a downhole fluid comprising:
 a flexural piezoelectric resonator associated with the downhole tool and disposed in the downhole fluid;
 a controller that actuates the flexural piezoelectric resonator at a frequency;
 a monitor that measures electrical impedance versus the frequency of the flexural piezoelectric resonator; and
 a processor that estimates the property of the downhole fluid from the measured electrical impedance.

25. The downhole tool of claim 24, wherein the frequency is a swept frequency and the processor estimates the property of the downhole fluid from the measured electrical impedance versus the swept frequency.

26. The downhole tool of claim 24, wherein the property of the downhole fluid comprises at least one of density and viscosity.

27. The downhole tool of claim 24, wherein the processor uses the property of the downhole fluid and at least one of the set consisting of a chemometric equation and a neural network to estimate a secondary property of the downhole fluid.

28. The downhole tool of claim 27, wherein the secondary property of the downhole fluid comprises nuclear magnetic resonance relaxation time.

29. The downhole tool of claim 24, wherein the flexural piezoelectric resonator comprises at least one of the set consisting of a bar bender, disk bender, cantilever, a tuning fork, micro-machined membrane and torsion resonator.

30. The downhole tool of claim 24, wherein the flexural piezoelectric resonator has a dimension smaller than an acoustic wavelength of the actuating frequency.

* * * * *